United States Patent [19]

Casper et al.

[11] Patent Number: 5,415,162
[45] Date of Patent: May 16, 1995

[54] MULTI-DOSE DRY POWDER INHALATION DEVICE

[75] Inventors: Robert A. Casper, Raleigh, N.C.;
Malcolm E. Taylor, Pelham, N.H.;
Frank A. Leith, Chapel Hill, N.C.;
David H. Leith, Chapel Hill;
Maryanne G. Boundy, Chapel Hill, N.C.

[73] Assignee: Glaxo Inc., Research Triangle Park, N.C.

[21] Appl. No.: 183,283

[22] Filed: Jan. 18, 1994

[51] Int. Cl.⁶ .................................... A61M 15/00
[52] U.S. Cl. ........................... 128/203.12; 128/203.21; 604/58
[58] Field of Search ................. 128/203.12, 203.15, 128/203.18, 203.19, 203.21, 200.14, 205.29; 222/81, 82, 630; 609/58

[56] References Cited

U.S. PATENT DOCUMENTS

| | | | |
|---|---|---|---|
| 3,967,761 | 7/1976 | Melton, Jr. et al. | 222/635 |
| 5,161,524 | 11/1992 | Evans | 128/203.15 |
| 5,192,548 | 3/1993 | Velasquez et al. | 128/203.12 |
| 5,207,217 | 5/1993 | Cocozza et al. | 128/203.21 |
| 5,239,993 | 8/1993 | Evans | 128/203.15 |
| 5,301,666 | 4/1994 | Lerk et al. | 128/203.15 |
| 5,337,740 | 8/1994 | Armstrong et al. | 128/203.15 |
| 5,349,947 | 9/1994 | Newbowe et al. | 604/58 |

Primary Examiner—Edgar S. Burr
Assistant Examiner—Virendra Srivastava
Attorney, Agent, or Firm—Richard E. Jenkins

[57] ABSTRACT

A breath-actuated dry powder medicament inhalator device having a housing and a conduit mounted within the housing defining an air passageway therethrough having an aperture in the sidewall thereof. A blister-type strip of sealed containers arranged in a matrix of rows and columns wherein the columns extend generally diagonally to the longitudinal axis of the strip is secured in a two-piece cage adapted for being rotatably mounted around the conduit of the inhalator device. Advancement means are provided for rotatably moving the two-piece cage and blister strip contained thereby in a generally helical pathway relative to the conduit so as to successively advance each of the sealed containers of the blister strip into registration with the conduit aperture. Piercing means are associated with the housing for successively piercing each of the sealed containers of the blister strip when advanced into registration with the conduit aperture by the advancement means in order to introduce the dry powder compound contained therein into the air passageway of the conduit.

33 Claims, 10 Drawing Sheets

MULTI-DOSE DRY POWDER INHALATION DEVICE

Technical Field

This invention relates to an inhalator device for the inhalation of medicament in dry powder form, and more particularly to a multi-dose dry powder inhalation device for administering multiple doses of medicament from a blister-type strip.

Related Art

As is well known to those skilled in the art, there are essentially two general classes of inhalation devices currently being offered in the marketplace for bronchial administration of a dose of dry powder medicament. The first class of device is characterized by using a pressurized aerosol propellant for the inhaler which discharges a metered dose of a medication suspended in a pharmaceutically inert liquid propellant such as fluorocarbon. This class of inhalation device has the characteristic of consistently delivering a predetermined dose of medication. However, the particles of medication are propelled at a high velocity from the metering valve, and there is a propensity for some of the medication to be deposited on the back of the mouth and in the throat of a user. Accordingly, these devices suffer the disadvantage that while a consistent, metered dose leaves the valve of the device, the effective dose entering the lungs of a user can vary with the shape and physical dimensions of the user's oral cavity and his ability to coordinate his breathing with the discharge of the medication.

The second class of generally known inhalation devices utilize a user's inhaled breath as a vehicle to transport a dry powder drug dosage. However, these devices also suffer certain shortcomings which are well known to one skilled in the art. A significant disadvantage of the second class of inhalation devices is a lack of an air flow velocity regulating means that can result in excessive inhalation velocity during use of the devices. Accordingly, these devices also suffer the disadvantage that the excessive inhalation velocity can cause the dry powder drug being inhaled to impinge upon the back of the mouth and the throat and to be thwarted from completing the desired journey to the lungs of a user.

Also, and very importantly, the second class of inhalation device suffers an additional shortcoming of not providing a large enough number of doses if a sealed compartment is utilized to transport the dry powder medicament to the site of dispersion. Alternatively, if the dry powder medicament is contained in a reservoir in order to provide a high number of doses of medicament, it is well known that moisture in most dry powder medicaments will tend to cause agglomeration and clumping of the dry powder which act to inhibit dispersion of the dry powder when introduced into the airflow of an inhalator device during inhalation by a user. Accordingly, the reservoir-type of inhalator device suffers from the disadvantage of being periodically rendered substantially unusable by becoming clogged by the agglomerated dry powder medicament. Thus, there is a long-felt need for a high dose dry powder inhalator that is easy to use and does not suffer from the problems and shortcomings of inhalators described hereinabove.

Representative of the reservoir-type of dry powder inhalation device is the TURBUHALER ® which is marketed by AB Astra in Europe and the subject matter of U.S. Pat. Nos. 4,524,769 and 4,907,583 (assigned to A. B. Draco of Sweden). This dry powder medicament inhaler device was developed for the delivery of small quantities of pharmacologically active dry powder compounds without the necessity for any carrier compound. The breath-actuated inhalator comprises a dosing unit constructed as a disk (with groups of conical holes for the drug compound) which is positioned at the bottom of a drug compound storage unit. The larger diameter bottom areas of the truncated cones of the disk oppose the storage unit so as to facilitate filling thereof during the loading and emptying of the dosing unit at inhalation.

Dosing is accomplished by rotating the dosing unit in the storage unit toward a pressure plate beneath the dosing unit. Plastic scrapers over the dosing units serve to load the holes with the drug compound, and dosing is performed by merely twisting the turning grip back and forth. Thus, when a user inhales through the inhaler device, the air enters a channel in the operating unit and passes through a hole in the pressure plate and through the dosing unit for release of the dose loaded in certain conical holes exposed to the area of the inhalation channel. Dry powder drug aggregates are broken up by the turbulent air flow in the inhalation channel and by the inserts in the nozzle mouthpiece. The non-refillable and non-reusable TURBUHALER ® inhalator can provide up to 200 doses prior to disposal thereof. However, as is well known in the inhalator art, this type of multiple dose inhaler suffers from a number of shortcomings including potentially significant dosage variability.

Another inhalator device of interest is disclosed in U.S. Pat. No. 5,161,524 assigned to Glaxo Inc. The inhalator device disclosed therein is a significant advancement in the second class of inhalators since it provides for a metered dose dosage inhaler with an automatic regulating means to provide a substantially constant predetermined maximum airflow velocity therethrough in order to minimize impingement of dry powder medicament at the back of the upper throat. The apparatus disclosed and claimed in the aforementioned patent is a very advantageous advancement in the inhalator art, but utilizes a relatively complex diaphragm mechanism to regulate airflow velocity and also is potentially subject to the agglomeration tendency of all large reservoir multi-dose dry powder inhalator devices.

The limitations of prior art dry powder medicament inhalator devices have now been overcome by the reusable, high dosage inhalator device of the present invention.

Disclosure of the Invention

Therefore, in accordance with the present invention, applicant provides a multi-dose inhaler device for administering a predetermined dose of dry powder compound from a blister-strip of sealed containers of dry powder compound wherein the portable inhalator device is adapted for reuse. The inhalator device comprises a housing having a conduit mounted therein which defines an air passageway therethrough, an air inlet end, an air exit end and an aperture extending through the side wall of the conduit between the ends thereof. A blister strip of sealed containers is provided wherein the sealed containers are arranged in a matrix of rows and columns and wherein the columns extend generally diagonally to the longitudinal axis of the strip. Cage means are provided for rotatably mounting the blister-type strip of sealed containers of dry powder compound in a cylindrical configuration around the conduit wherein the rows of the blister-type strip extend generally parallel to the longitudinal axis of the conduit.

The inhalator device further includes advancement means associated with the housing for rotatably moving the cage means in a generally helical pathway relative to the conduit so as to successively advance each of the sealed containers of the blister-type strip into registration with the aperture of the conduit. Finally, piercing means associated with the housing are provided for piercing each of the sealed containers of the blister strip when advanced into registration with the aperture of the conduit so as to introduce the dry powder compound into the air passageway of the conduit. Thus, the blister-type strip will be rotatably and axially moved relative to the conduit as said sealed containers thereof are advanced along a helical pathway and then successively pierced for administration of a predetermined amount of the dry powder compound from the inhalator device.

It is therefore the object of the present invention to provide an improved multi-dose dry powder inhalator device.

It is another object of the present invention to provide an improved multi-dose dry powder inhalator device which obviates problems associated heretofore with high dosage dry powder inhalator devices.

It is another object of the present invention to provide an improved dry powder inhalator device which utilizes a blister-type strip of sealed containers of the dry powder compound wherein the sealed compartments of the dry powder compound are successively advanced from the first to the last sealed compartment contained within the strip.

It is yet another object of the present invention to provide an improved multi-dose dry powder inhalator device which simply and efficiently administers a high number of metered doses of a dry powder compound and which may be reused subsequent to exhaustion of the dry powder compound doses carried thereby.

Some of the objects of the invention having been stated hereinabove, other objects will become evident as the description proceeds, when taken in connection with the accompanying drawings.

Best Mode for Carrying Out the Invention

As used in the specification of the instant application, the term "dry powder medicament" means a dry powder substance used to achieve a therapeutic effect in respiratory therapy. The term "multi-dose dry powder inhalator" used herein means a device that is capable of delivering multiple doses of dry powder medicament without requiring refilling of the device. Also, although the dry powder inhalator device of the instant invention is shown as a device adapted primarily for oral inhalation, it should be appreciated that the invention contemplates inhalator devices that may also be adapted for nasal inhalation of dry powder compounds or medicaments.

Figure 6:
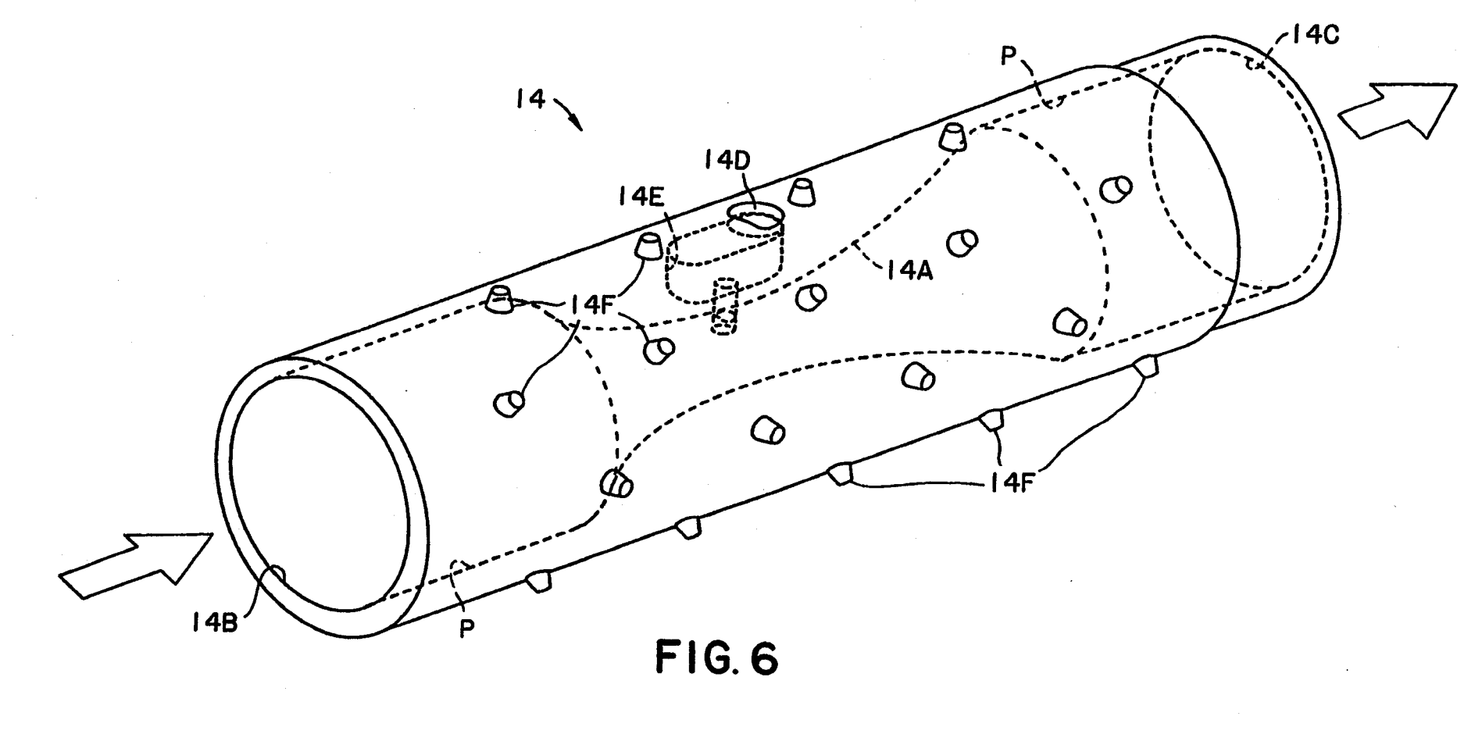
FIG. 6 is a perspective view of the air passageway conduit contained within the housing of the inhalator device of the present invention.
Figure 6A:
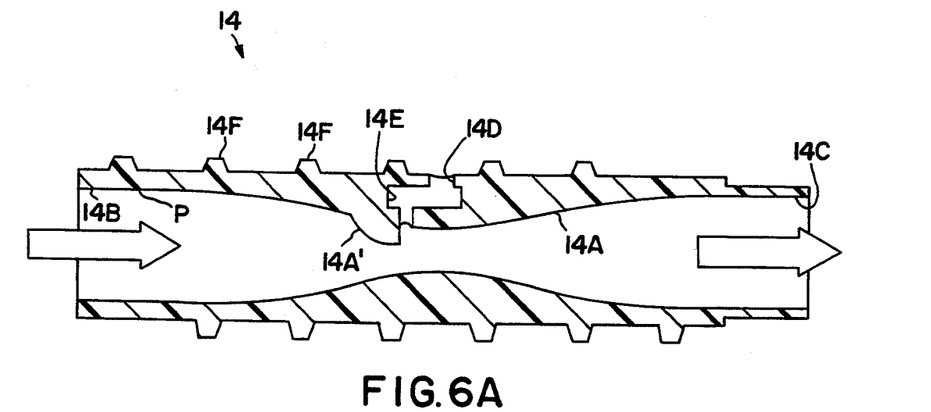
FIG. 6A is a vertical cross sectional view of the air passageway conduit contained within the housing of the inhalator device of the present invention.

Referring now more specifically to the drawings, a preferred embodiment of a dry powder dosage inhalator device according to the present invention is shown in FIGS. 1-9 and generally designated 10. Inhalator device 10 comprises a housing 12 having an air passageway conduit 14 secured in the central portion thereof. Conduit 14 (see FIGS. 1, 6 and 6A) defines an air passageway therethrough and most suitably has a venturi 14A in the medial portion thereof between the air inlet end 14B and air exit end 14C (which is adapted to be inserted into the mouth of a user). Although venturi 14A is depicted in the preferred embodiment of inhalator device 10, applicant contemplates that inhalator device 10 could also be constructed without 14A in conduit 14 and still function with an acceptable degree of efficacy.

An aperture 14D is provided in the side wall of the air passageway P so as to extend from the outside surface of conduit 14 to the inside venturi portion 14A of air passageway P. A swirl chamber 14E is provided between aperture 14D and venturi portion 14A for assuring deaggregation of the dry powder medicament which is urged into aperture 14D in a manner which will be described in detail hereinafter. Most suitably, a ramp 14A' is provided within venturi 14A and adjacent the internal end of aperture 14D to disrupt air flow so as to create localized mixing of air and the dry powder medicament (see FIG. 6A). Conduit 14 also includes a plurality of frusto-conical protuberances 14F on the outer surface thereof which are arranged in a helix extending generally around the longitudinal axis of conduit 14 and which serve a function to also be described in detail hereinafter.

Housing 12 further includes an advancement mechanism generally designated 16 and a button actuated piercing mechanism generally designated be for piercing a sealed compartment of a blister strip in order to introduce the dry powder medicament contained therein into the passageway P of conduit 14.

A blister strip or pack 20 (see particularly FIGS. 1, 2 and 4) is provided which is sufficiently flexible to be rolled from an initially flat configuration into a cylindrical configuration. Blister strip 20 most suitably is formed from soft aluminum having cold formed cavities 20A therein filled with the dry powder medicament and an adhesive-coated aluminum lid stock 20B secured to the top thereof. Blister strip 20 may also be formed from a polymer such as fluoropolymer which is adaptable to thermo-vacuum processing in order to form cavities 20A with the adhesive-coated aluminum lid 20B provided thereon. Lid 20B and cavities 20A of blister strip 20 are of necessity formed so as to be capable of being penetrated by button-actuated piercing mechanism 18 to be described hereinafter. Also, and very significantly to the instant invention, it can be seen with particular reference to FIG. 2 that cavities 20A of blister strip 20 are formed in a matrix wherein the rows extend normally to the longitudinal axis of the strip and the columns extend parallel to each other and diagonally to the longitudinal axis of the strip so as to extend helically around the axis of a cylinder formed with the flexible strip. Most suitably blister strip 20 contains either 60 or 120 doses of dry powder medicament within cavities 20A although other dosage levels are within the contemplated scope of the present invention.

Referring now particularly to FIGS. 1, 2, 3 and 5, a two-piece blister cage generally designated 30 is shown which serves to support each dose-containing cavity 20A of blister strip 20 in a nesting relationship. More specifically, cage 30 is formed from a flexible inner cage 32 constructed of flat segments 32A, each containing molded receptacles or nests 32B therein for receiving a row of cavities 20A of blister strip 20. Segments 32A defining nests 32B therein are pivotably formed together with a suitable molded hinge 32C between each of segments 32A to allow for forming of a cylindrical cage from an initially flat strip of segments 32A. Nests 32B of inner cage 32 each define an aperture or opening 32B' in the bottom thereof.

Figure 1:
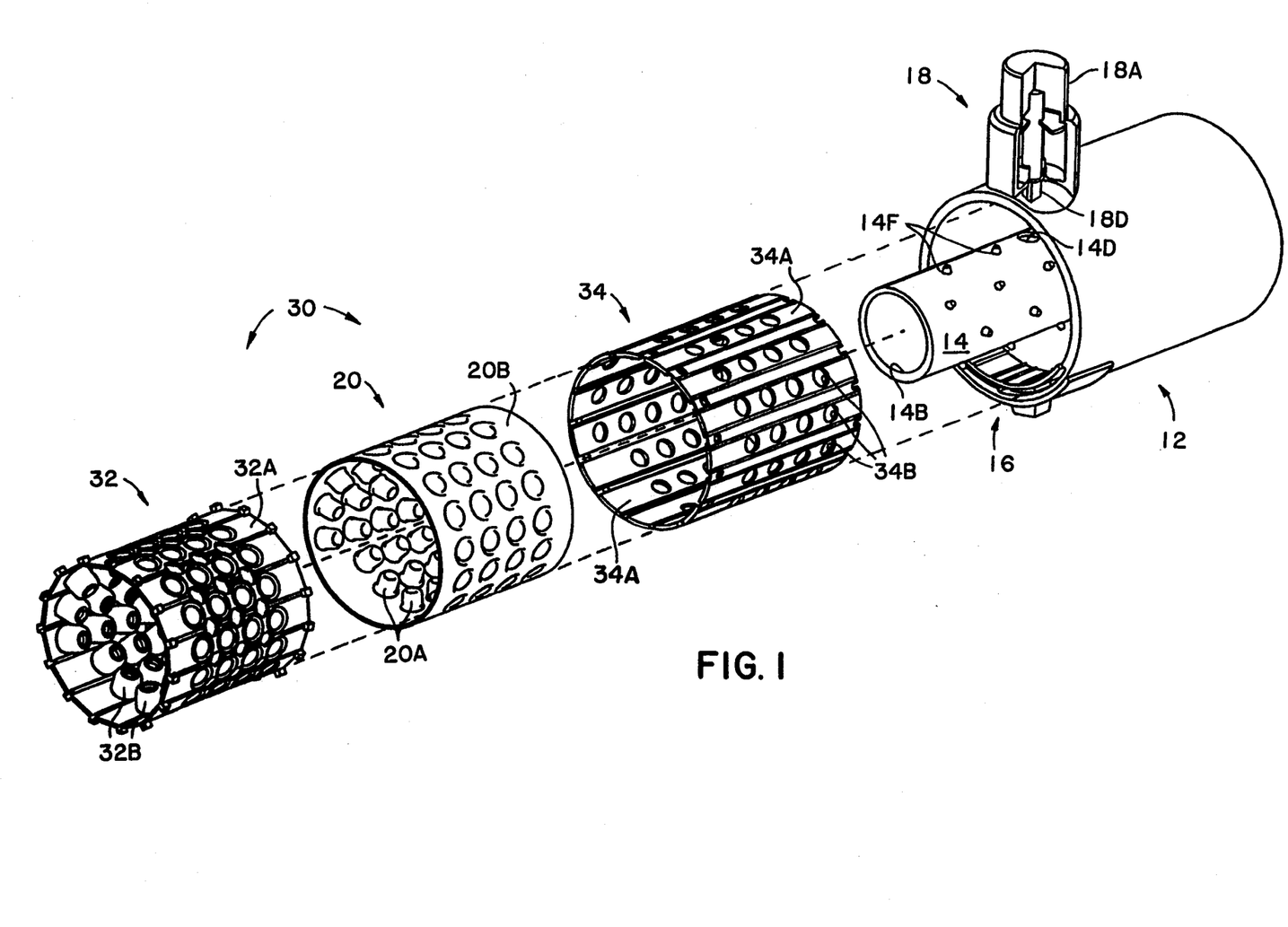
FIG. 1 is an exploded perspective view, with parts broken away, of the inhalator device of the invention.
Figure 2:
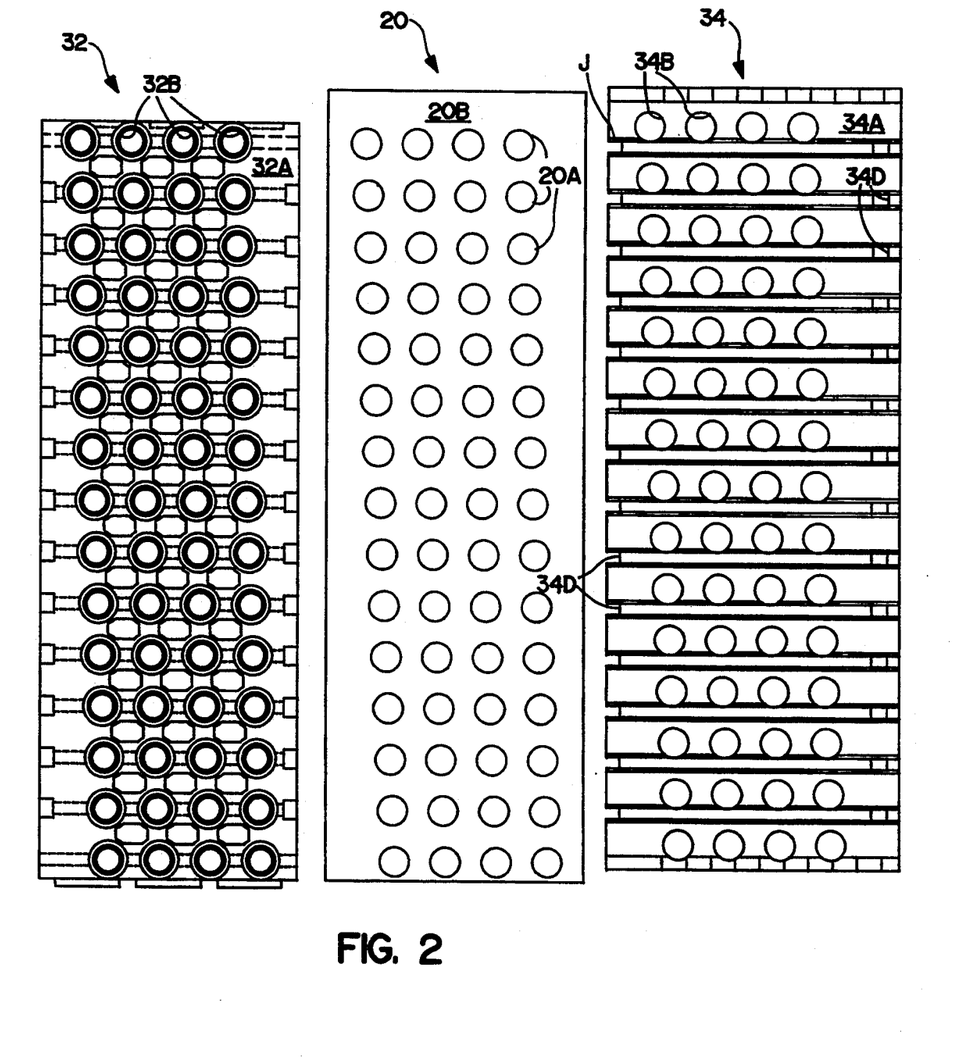
FIG. 2 is a top plan view of the first cage element, blister strip and second cage element utilized in the disposable multi-dose package assembly contemplated for use with the inhalator device of the invention.
Figure 3:
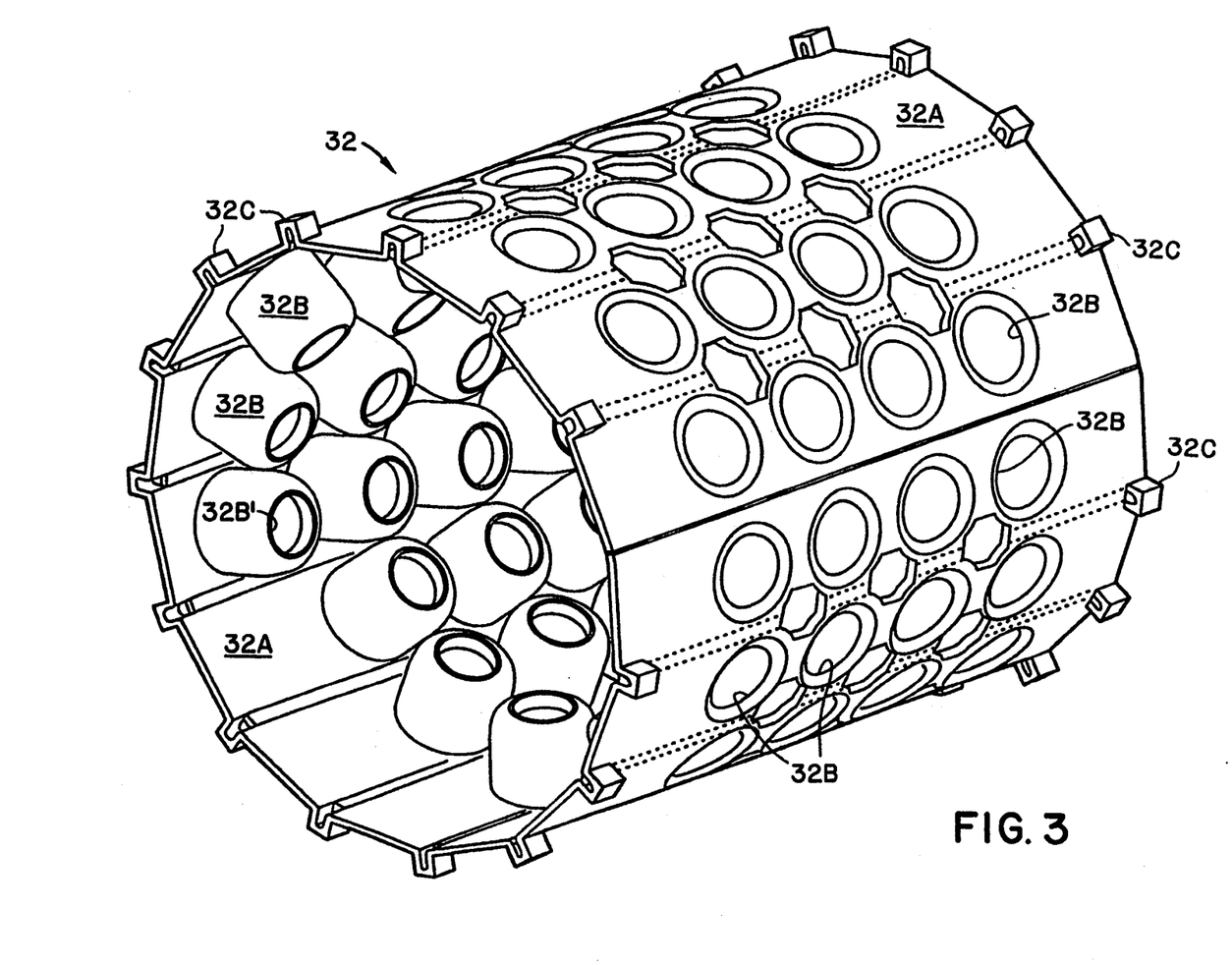
FIG. 3 is a perspective view of the first cage element of the inhalator device of the invention.
Figure 4:
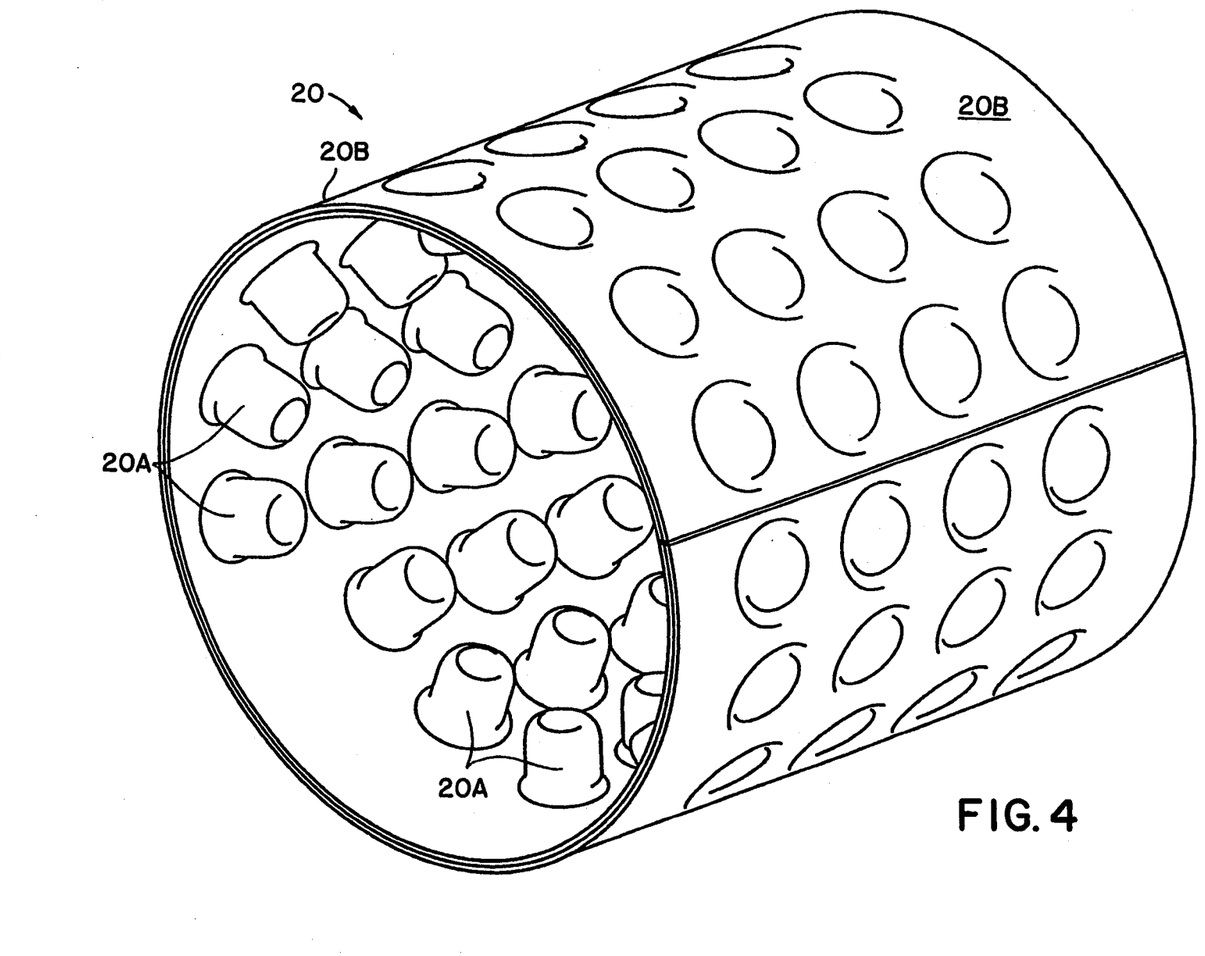
FIG. 4 is a perspective view of the blister strip of dry powder compound for use with the inhalator device of the invention.
Figure 5:
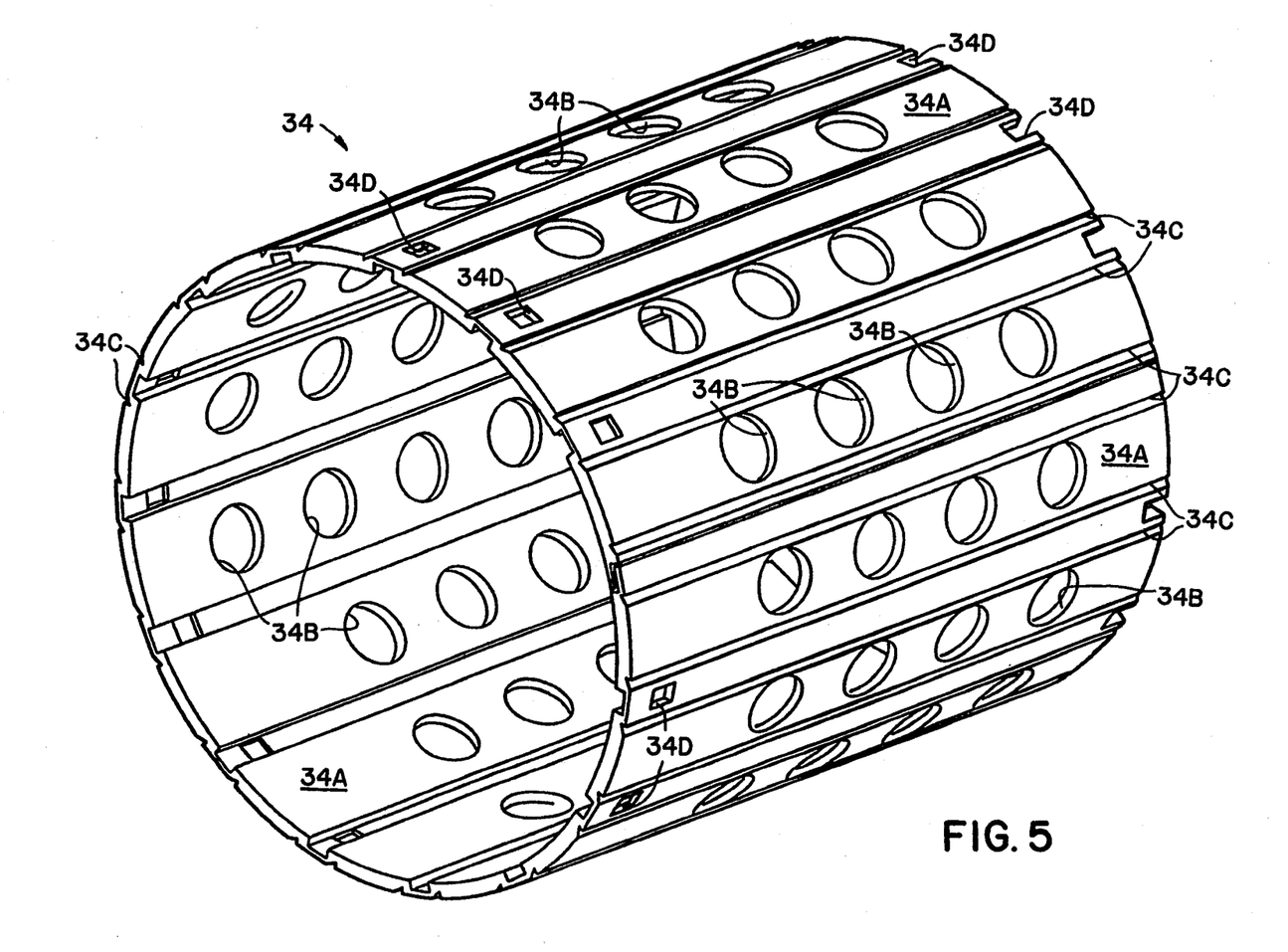
FIG. 5 is a perspective view of the second cage element for use with the inhalator device of the present invention.

Although other configurations are possible, most suitably inner cage 32 serving to nest blister pack 20 therein will consist of 15 segments 32A containing rows of either four or eight blister cavity nests 32B. Notches 32C are provided adjacent each end of segments 32A to interlock with outer cage or sleeve 34 in a manner to be described hereinbelow. Most suitably inner cage element 32 is formed from polypropylene in the flat condition but capable of being formed into a cylindrical configuration after assembly with blister pack 20 and outer cage 34.

Outer cage or sleeve 34 is also formed as a flexible strip which can be formed into a cylindrical shape as required. Outer cage 34 is formed as an integral unit most suitably defining 15 raised portions 34A corresponding to the 15 segments 32A of inner cage 32. Raised portions 34A extend horizontally across the width of outer cage 34 and most suitably define either four or eight apertures 34B therein which are in vertical registration with a respective row of cavities 20A of blister strip 20 which reside in a corresponding row of nests 32B of inner cage 32. Outer cage element 34 further defines (most suitably) 15 pairs of ratchet teeth 34C provided between the raised portions 34A thereof to provide for rotational movement of outer cage element 34 by advancement mechanism 16. Outer cage element 34 also is formed so that the ends thereof may be snapped together by suitable means (not shown) in order to form a joint J (see FIG. 5) to hold former flat outer cage element 34 in a cylindrical configuration as desired. Outer cage element 34 is provided with apertures 34D adjacent each end of raised portions 34A to facilitate assembly with inner cage 32 by serving to interlockingly receive corresponding notches 32C of said inner cage 32. Similarly to inner cage 32, outer cage 34 is preferably formed from polypropylene, although other materials could be used for fabrication thereof.

Figure 8:
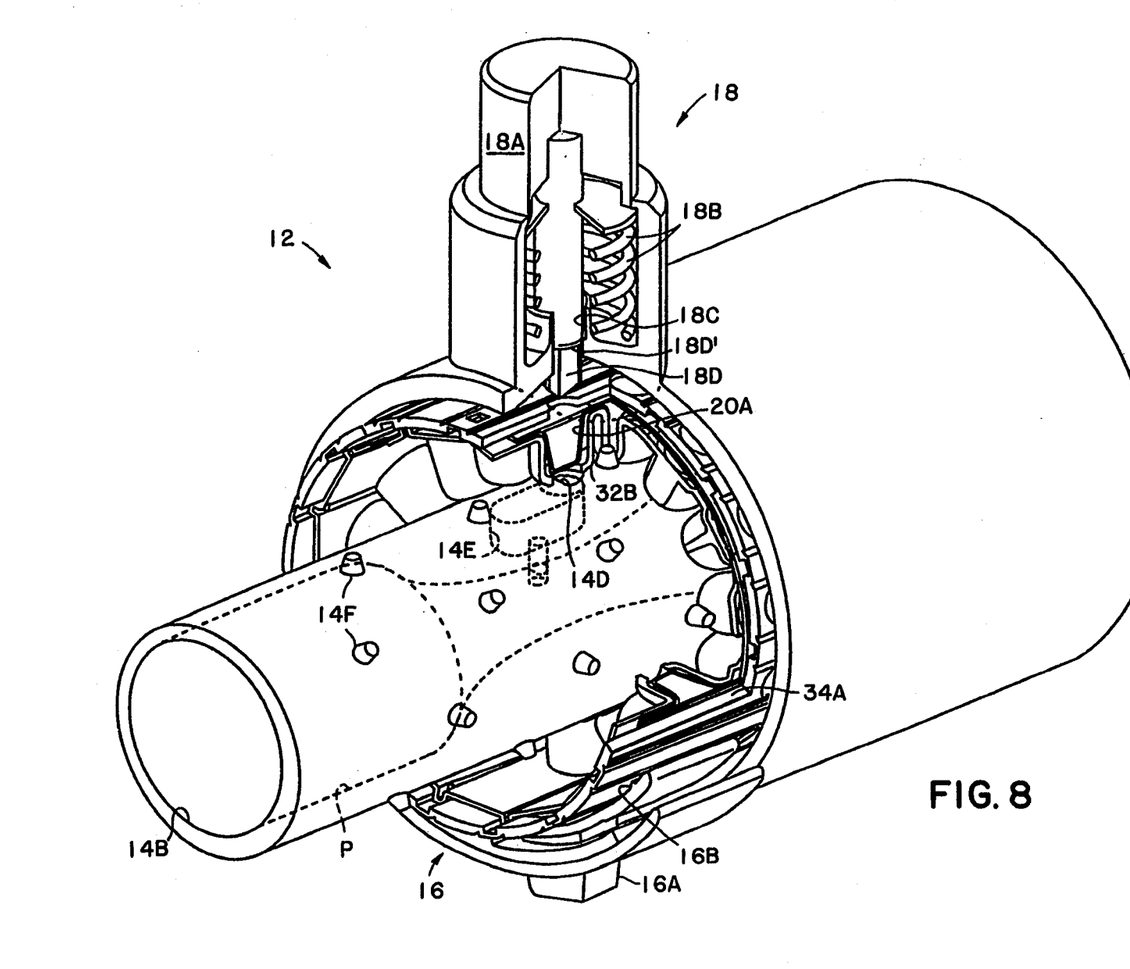
FIG. 8 is a perspective view, with parts broken away, of the inhalator device of the present invention.
Figure 9A:
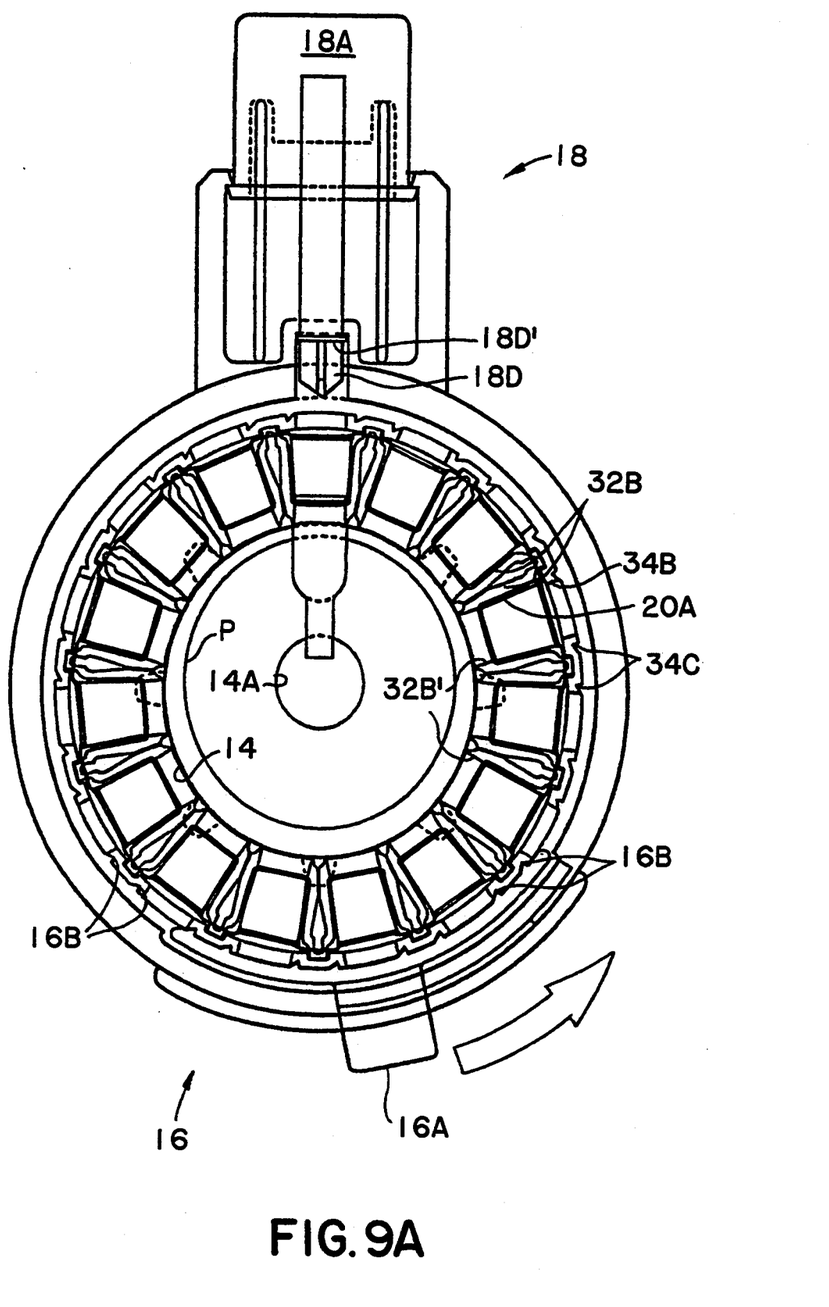
FIGS. 9A and 9B are front elevation views of the inhalator device of the invention prior to depression of the drug administration button and subsequent to depression of the drug administration button, respectively.
Figure 9B:
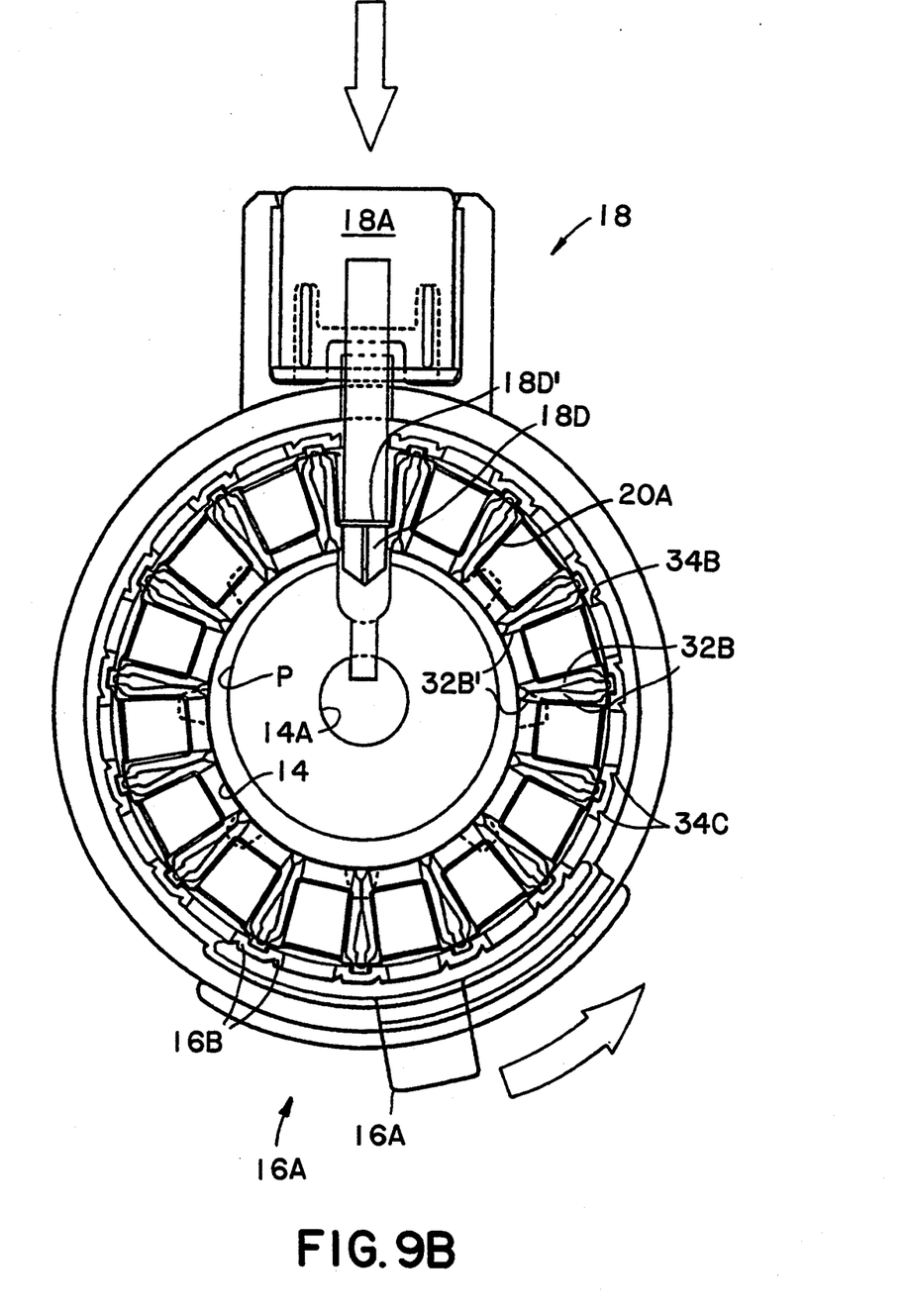

Referring now to FIGS. 8 and 9A, 9B, button actuated piercing mechanism be will be described in more detail. Mechanism be comprises button LeA which is urged into its normally raised position by spring 18B. Secured to button 18A and extending vertically downwardly therefrom and through an aperture 18C in housing 12 is a hollow needle or cannula 18D. Cannula 18D is positioned so as to be in vertical registration with aperture 14D of conduit 14 (see FIG. 6). Thus, as advancement mechanism 16 (to be described in detail hereinafter) serves to rotate successive dry powder medicament-filled cavities 20A of blister strip 20 into vertical registration with conduit aperture 14D, cannula 18D is positioned for downward vertical actuation in order to: (1) traverse through an aperture 34B of outer cage element 34; (2) pierce protective lid 20B and cavity 20A of blister strip 20 thereunder; and to (3) force the dry powder medicament through the bottom of a corresponding nest 32B of inner cage 32 and into aperture 14D of conduit 14.

In order to provide a repeatable dry powder medicament flow from ruptured cavity 20A of blister strip 20 through to swirl chamber 14E of conduit 14, a good seal must be provided between the bottom of blister strip cavity 20A and corresponding inner cage nest 32B, as well as between the bottom of inner cage nest 32B and aperture 14D leading to swirl chamber 14E of conduit 14. This seal is effected through finger pressure which is maintained on button 18A so as to press the shoulder 18D' of cannula 18D against the inside of blister strip cavity 20A. A molded seal face will be provided on exit hole 32B' from nests 32B of inner cage 32 which will have sufficient flexibility to seal each nest to aperture 14D of conduit 14 when the nest is in operative engagement therewith. Most suitably, there is also a spherical molded surface around aperture 14D to facilitate a positive seal. Thus, as the applicant maintains downward pressure on button 18A, air will enter and pass through the central opening of cannula bed and through conduit aperture 14B in order to facilitate swirling of the dry powder medicament in swirl chamber 14E and introduction thereof into venturi portion 14A of air passageway P. Ambient air will be allowed to enter cannula 18D through suitable openings (not shown) in the button and housing of button-actuated piercing mechanism 18. Most suitably, cannula 18D will be formed from steel and press fed into button 18A which will be formed from polystyrene. Spring 18B will most suitably be a conventional stainless steel compression spring.

FIG. 9A illustrates button-actuated piercing mechanism 18 in its inoperative raised position and FIG. 9B illustrates button-actuated piercing mechanism 18 in its operative depressed position wherein cannula 18D has pierced a blister strip cavity 20A and introduced the dry powder medicament contained therein into venturi portion 14A of passageway P within conduit 14.

Finally, with particular reference to FIGS. 8 and 9A, 9B, the advancement mechanism 16 of inhalator device 10 will be described in detail. Advancement mechanism 16 consists of a reciprocatingly mounted button 16A which is adapted to engage four pairs of ratchet teeth 34C of outer cage element 34 with four pairs of corresponding teeth 16B and to rotate the cage assembly consisting of inner cage 32, blister strip 20 and outer cage 34 one row over (counterclockwise) with respect to hollow piercing cannula 18D of button-actuated piercing mechanism 18 and conduit aperture 14D. A fixed stop will prevent reverse rotation and a spring (not shown) will serve to reset advancement mechanism 16 to its original position. Advancement mechanism 16 may be of any suitable design to engage outer cage element 34, rotate same one row, and disengage outer cage element 34 and reset for another indexing movement as desired by a user. Although other materials may be utilized, advance mechanism 16 is preferably fabricated from nylon for extended wear resistance and the return spring (not shown) formed from a suitable urethane.

Thus, it can be appreciated that due to the unique matrix of blister strip cavities 20A and the cooperative engagement of the undersides of nests 32B of inner cage 32 with the helically arranged protuberances 14F on the outer surface of conduit 14, blister strip cavities 20A will move in a helical pathway around conduit 14 and be successively presented from first to last cavity 20A to piercing cannula 18D and conduit aperture 14D therebeneath during the course of multi-dosing of a dry powder medicament by a user.

Figure 7A:
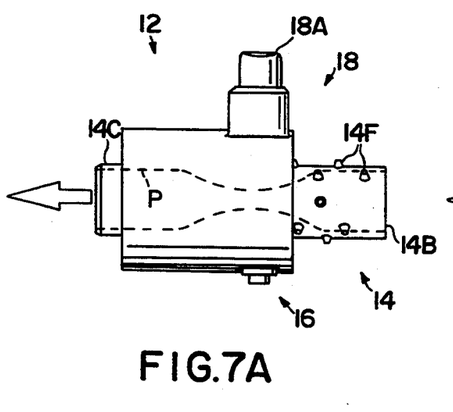
FIGS. 7A and 7B are side elevation views of the inhalator device of the present invention prior to administration and subsequent to administration, respectively, of the multiple dry powder doses contained within the blister-type strip.
Figure 7B:
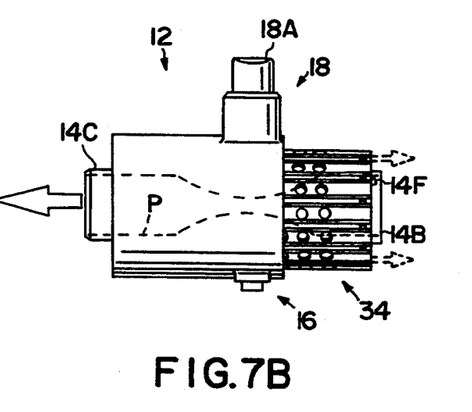

For better understanding, FIG. 7A depicts inhalator device 10 with blister strip 20 in its unused position and FIG. 7B depicts inhalator device 10 subsequent to exhaustion of the entire 60 doses of dry powder medicament contained in blister strip cavities 20A. As can be appreciated, the assembly of inner cage 32, blister strip 20 and outer cage 34 has helically advanced from within housing 12 to a position substantially outside of housing 12 during the course of multiple dosing with inhalator device 10 of the instant invention. To reiterate, blister strip 20 is caused to helically advance around conduit 14 by the interaction of protuberances 14F on the outer surface of conduit 14 with the undersides of nests 32B of inner cage 32 (the columns of which define four helical pathways to movably contact protuberances 14F of conduit 14).

In use, applicant contemplates that inner cage 32, blister strip 20 and outer cage 34 would be obtained from a pharmacy or the like and be a disposable part of reusable inhalator device 10. The aforementioned elements would be procured in a flat state for ease of packaging, etc. and assembled according to the description provided hereinabove. The assembly of inner cage 32, blister strip 20 and outer cage 34 would then be formed into a cylindrical disposable cartridge which would be inserted into inhalator device 10 by squeezing housing 12 into a slightly oval shape to prevent engagement by advancement mechanism 16 as the assembly is screwed fully into position over conduit 14. Thereafter, advancement mechanism 16 would be utilized to successively advance the individual cavities 20A of blister strip 20 into a properly indexed position with button-actuated piercing mechanism 18 to facilitate dosing by a user. Once all of the doses in the blister strip have been administered (preferably either a 60 dose or a 120 dose blister strip), the spent disposable assembly would be merely rotated several more turns in the indexing direction (counter-clockwise) in order to remove the assembly from inhalator device 10 for disposal thereof.

It will thus be seen that there has been described a novel multi-dose dry powder inhalator device which is designed to easily and simply provide a high number of dry powder medicament doses from a blister strip package without the disadvantages suffered by presently known dry powder medicament inhalator devices.

It will be understood that various details of the invention may be changed without departing from the scope of the invention. Furthermore, the foregoing description is for the purpose of illustration only, and not for the purpose of limitation—the invention being defined by the claims.

What is claimed is:

1. A portable device for the inhalation of a predetermined amount of dry powder compound from a blister-type strip of sealed containers, comprising:
   (a) a housing;
   (b) a conduit mounted within said housing defining an air passageway therethrough and having an air inlet end and an air exit end and an aperture extending through a side wall of said conduit therebetween, said air exit end being adapted for insertion into the mouth of a user;
   (c) a blister-type strip of sealed containers wherein said sealed containers are arranged in a matrix of rows and columns and said columns extend generally diagonally to the longitudinal axis of said strip;
   (d) cage means for rotatably mounting said blister-type strip of sealed containers of dry powder compound in a cylindrical configuration around said conduit wherein said rows of said blister-type strip extend generally parallel to the longitudinal axis of said conduit;
   (e) advancement means associated with said housing for rotatably moving said cage means in a generally helical pathway relative to said conduit so as to successively advance each of said sealed containers of said blister-type strip into registration with the aperture of said conduit; and
   (f) piercing means associated with said housing for piercing each of said sealed containers of said blister strip when advanced into registration with the aperture of said conduit so as to introduce said dry powder compound therein into the air passageway of said conduit;

whereby said blister-type strip will be rotatably and axially moved relative to said conduit as said sealed containers thereof are advanced along said helical pathway and successively pierced for administration of a predetermined amount of said dry powder compound from said inhalation device.

2. A portable device according to claim 1 wherein said housing defines a generally cylindrical shape having a longitudinal axis extending generally coaxially with the longitudinal axis of said conduit.

3. A portable device according to claim 2 wherein the inside surface of said, housing is radially spaced apart from the outside surface of said conduit so as to define a space therebetween for receiving said cage means.

4. A portable device according to claim 2 wherein said housing defines an opening around the circumference of said air inlet end of said conduit so as to receive said cage means therethrough.

5. A portable device according to claim 1 wherein said air passageway defined within said conduit comprises a venturi in the medial portion of the length thereof, and said aperture extending through said conduit has one end on the outside surface of said conduit and the other end opens into said venturi of said conduit.

6. A portable device according to claim 5 wherein said aperture of said conduit includes an enlarged swirl chamber between said inlet end and said outlet end thereof.

7. A portable device according to claim 1 wherein said blister-type strip comprises 15 rows of sealed containers extending generally normally to the longitudinal axis of said strip and 4 columns of sealed containers each extending generally parallel to each other and diagonally to the longitudinal axis of said strip.

8. A portable device according to claim 1 wherein said blister-type strip comprises 15 rows of sealed containers extending generally normally to the longitudinal axis of said strip and 8 columns of sealed containers each extending generally parallel to each other and diagonally to the longitudinal axis of said strip.

9. A portable device according to claim 1 wherein said cage means comprises:
- a first flexible strip defining a plurality of cavities therein so that when said blister-type strip is placed in overlying relationship thereto said sealed containers of said blister-type strip will each nest in a corresponding one of said plurality of cavities of said first strip;
- a second flexible strip defining a plurality of apertures therein so that when said second strip is placed in overlying relationship to said blister-type strip and said first strip, said apertures of said second strip will each be in vertical registration with a corresponding one of said sealed containers of said blister-type strip;
- said first and second strips being adapted to be secured together as an assembly with said blister-type strip positioned therebetween and said assembly then formed into a cylindrical configuration for positioning around said conduit.

10. A portable device according to claim 9 wherein said cage means is disposable.

11. A portable device according to claim 1 wherein said advancement means comprises:
- a plurality of protuberances arranged in a helix on the outside surface of said conduit defining said air passageway and serving to guide the movement of said cage around said conduit along the helical pathway defined by said protuberances; and
- ratchet means reciprocatingly mounted to said housing and adapted to cooperatively engage said cage means and to rotate said cage means about said conduit a sufficient distance to advance the next successive row of sealed containers of said blister-type strip such that one of said sealed containers thereof will be in registration with the aperture of said conduit.

12. A portable device according to claim 1 wherein said piercing means comprises a needle element adapted for vertical movement from a retracted position to an extended position wherein said needle element pierces said sealed container in registration with the aperture of said conduit.

13. A portable device according to claim 12 wherein said piercing means comprises an air vent therein to allow for air entry into said air passageway of said conduit from outside said housing subsequent to piercing of said sealed container by said needle element.

14. In a portable device for the inhalation of a predetermined amount of dry powder compound and characterized by a housing; an air passageway provided within said housing having an air inlet end, an air exit end adapted for insertion into the mouth of a user, and an aperture through a side wall at a predetermined location along the length thereof; and piercing means associated with said housing for piercing a sealed container of said dry powder compound when positioned in registration with the aperture of said air passageway so as to introduce said dry powder compound into the air passageway, the improvement comprising:
- a blister-type strip of sealed containers of dry powder compound arranged in a matrix of rows and columns wherein said columns extend generally parallel to each other and generally diagonally to the longitudinal axis of said strip;
- cage means for rotatably mounting said blister-type strip of sealed containers in a cylindrical configuration within said housing and around said air passageway wherein said rows of said blister-type strip extend generally parallel to the longitudinal axis of said air passageway; and
- advancement means associated with said housing for rotatably moving said cage means in a generally helical pathway relative to said air passageway so as to successively advance each of said sealed containers of said blister-type strip into registration with the aperture of said air passageway;

whereby said blister-type strip will be rotatably and axially moved relative to said air passageway as said sealed containers thereof are advanced along said helical pathway and successively pierced for administration of a predetermined amount of said dry powder compound from said inhalation device.

15. A portable device according to claim 14 wherein said air passageway is defined by a conduit and the inside surface of said housing is radially spaced apart from the outside surface of said conduit so as to define a space therebetween for receiving said cage means.

16. A portable device according to claim 15 wherein said housing defines an opening around the circumference of said air inlet end of said conduit so as to receive said cage means therethrough.

17. A portable device according to claim 14 wherein said blister-type strip comprises 15 rows of sealed containers extending generally normally to the longitudinal axis of said strip and 4 columns of sealed containers each extending generally parallel to each other and diagonally to the longitudinal axis of said strip.

18. A portable device according to claim 14 wherein said blister-type strip comprises 15 rows of sealed containers extending generally normally to the longitudinal axis of said strip and 8 columns of sealed containers each extending generally parallel to each other and diagonally to the longitudinal axis of said strip.

19. A portable device according to claim 15 wherein said cage means comprises:
- a first flexible strip defining a plurality of cavities therein so that when said blister-type strip is placed in overlying relationship thereto said sealed containers of said blister-type strip will each nest in a corresponding one of said plurality of cavities of said first strip;
- a second flexible strip defining a plurality of apertures therein so that when said second strip is placed in overlying relationship thereto said blister-type strip and said first strip, said apertures of said second strip will each be in vertical registration with a corresponding one of said sealed containers of said blister-type strip;

said first and second strips being adapted to be secured together as an assembly with said blister-type strip positioned therebetween and said assembly then formed into a cylindrical configuration for positioning around said conduit.

20. A portable device according to claim 19 wherein said cage means is disposable.

21. A portable device according to claim 15 wherein said advancement means comprises:
a plurality of protuberances arranged in a helix on the outside surface of said conduit and serve to guide the movement of said cage around said conduit along the helical pathway defined by said protuberances;
ratchet means reciprocatingly mounted to said housing and adapted to cooperatively engage said cage means and to rotate said cage means about said conduit a sufficient distance to advance the next successive row of sealed containers of said blister-type strip such that one of said sealed containers thereof will be in registration with the aperture of said air passageway.

22. A portable device according to claim 21 wherein said advancement means successively helically advances said cage means and blister-type strip contained thereby from an innermost first position within the housing of said portable inhalation device to a second outermost position wherein at least a portion of said cage means and blister-type strip contained thereby are outside of the housing.

23. A portable device for the inhalation of a predetermined amount of dry powder compound from a blister-type strip of sealed containers, comprising:
(a) a housing;
(b) a conduit mounted within said housing defining an air passageway therethrough and having an air inlet end and an air exit end and an aperture extending through a side wall of said conduit therebetween, said air exit end being adapted for insertion into the mouth of a user;
(c) a blister-type strip of sealed containers wherein said sealed containers are arranged in a matrix of rows and columns;
(d) cage means for rotatably mounting said blister-type strip of sealed containers of dry powder compound in a cylindrical configuration around said conduit;
(e) advancement means associated with said housing for rotatably moving said cage means relative to said conduit so as to successively advance each of said sealed containers of said blister-type strip into registration with the aperture of said conduit; and
(f) piercing means associated with said housing for piercing each of said sealed containers of said blister strip when advanced into registration with the aperture of said conduit so as to introduce said dry powder compound therein into the air passageway of said conduit;
whereby said blister-type strip will be moved relative to said conduit as said sealed containers thereof are advanced and successively pierced for periodic administration of a predetermined amount of said dry powder compound from said inhalation device.

24. A portable device according to claim 23 wherein said housing defines a generally cylindrical shape having a longitudinal axis extending generally coaxially with the longitudinal axis of said conduit.

25. A portable device according to claim 24 wherein the inside surface of said housing is radially spaced apart from the outside surface of said conduit so as to define a space therebetween for receiving said cage means.

26. A portable device according to claim 24 wherein said housing defines an opening around the circumference of said air inlet end of said conduit so as to receive said cage means therethrough.

27. A portable device according to claim 23 wherein said air passageway defined within said conduit comprises a venturi in the medial portion of the length thereof, and said aperture extending through said conduit has one end on the outside surface of said conduit and the other end opens into said venturi of said conduit.

28. A portable device according to claim 27 wherein said aperture of said conduit includes an enlarged swirl chamber between said inlet end and said outlet end thereof.

29. A portable device according to claim 23 wherein said cage means comprises:
a first flexible strip defining a plurality of cavities therein so that when said blister-type strip is placed in overlying relationship thereto said sealed containers of said blister-type strip will each nest in a corresponding one of said plurality of cavities of said first strip;
a second flexible strip defining a plurality of apertures therein so that when said second strip is placed in overlying relationship to said blister-type strip and said first strip, said apertures of said second strip will each be in vertical registration with a corresponding one of said sealed containers of said blister-type strip;
said first and second strips being adapted to be secured together as an assembly with said blister-type strip positioned therebetween and said assembly then formed into a cylindrical configuration for positioning around said conduit.

30. A portable device according to claim 29 wherein said cage means is disposable.

31. A portable device according to claim 23 wherein said advancement means comprises:
a plurality of protuberances on the outside surface of said conduit defining said air passageway and serving to guide the movement of said cage around said conduit along a pathway defined by said protuberances; and
ratchet means reciprocatingly mounted to said housing and adapted to cooperatively engage said cage means and to rotate said cage means about said conduit a sufficient distance to advance said blister-type strip such that successive sealed containers thereof will be in registration with the aperture of said conduit.

32. A portable device according to claim 23 wherein said piercing means comprises a needle element adapted for vertical movement from a retracted position to an extended position wherein said needle element pierces said sealed container in registration with the aperture of said conduit.

33. A portable device according to claim 32 wherein said piercing means comprises an air vent therein to allow for air entry into said air passageway of said conduit from outside said housing subsequent to piercing of said sealed container by said needle element.

* * * * *